United States Patent [19]

Singerman

[11] 3,997,548
[45] Dec. 14, 1976

[54] HYDROXY-2,1-BENZISOTHIAZOLES

[75] Inventor: Gary M. Singerman, Prairie Village, Kans.

[73] Assignee: Gulf Research & Development Company, Pittsburgh, Pa.

[22] Filed: May 28, 1975

[21] Appl. No.: 581,635

Related U.S. Application Data

[62] Division of Ser. No. 426,118, Dec. 19, 1973, Pat. No. 3,929,815.

[52] U.S. Cl. .......................................... 260/304 A
[51] Int. Cl.$^2$ ..................................... C07D 275/04
[58] Field of Search ............................... 260/304 A

[56] References Cited

UNITED STATES PATENTS 3,187,001  6/1965  Meyer et al. ................. 260/304 A

*Primary Examiner*—R. Gallagher

[57] ABSTRACT

2,1-Benzisothiazolyl N-lower alkyl- or N,N-di-lower alkylcarbamates are prepared from novel hydroxy-2,1-benzisothiazoles and alkoxy-2,1-benzisothiazoles. 2,1-Benzisothiazol-4-yl N-methylcarbamate is an effective insecticide.

5 Claims, No Drawings

HYDROXY-2,1-BENZISOTHIAZOLES

This is a division of application Ser. No. 426,118 filed Dec. 19, 1973, now U.S. Pat. No. 3,929,815.

This invention relates to novel 2,1-benzisothiazoles having the general formula:

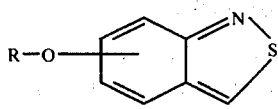

where R is hydrogen.

The 2,1-benzisothiazolyl N-lower alkyl- or N,N-di-lower alkylcarbamates are a new class of aromatic carbamates having significant pesticidal activity. These 2,1-benzisothiazolyl N-lower alkyl- or N,N-di-lower alkylcarbamates are prepared from a lower alkoxy-2-methylaniline or a lower alkoxy-2-methyl-N-sulfinylaniline in a three-stage reaction. The lower alkoxy-2-methylaniline or lower alkoxy-2-methyl-N-sulfinylaniline is reacted with an alkyl- or aryl-sulfinylsulfonamide such as methyl-, phenyl, or tolyl-sulfinylsulfonamide to cause ring closure and form the corresponding alkoxy-2,1-benzisothiazole. In the second reaction the alkoxy group is converted to a hydroxy group to form the hydroxy-2,1-benzisothiazole. In the third reaction the hydroxy group is converted to an N-lower alkyl- or N,N-di-lower alkylcarbamoyloxy group to produce the 2,1-benzisothiazolyl N-lower alkyl or N,N-di-lower alkylcarbamates.

As used herein lower alkyl means alkyl groups having one to four carbon atoms, including methyl, ethyl, propyl, isopropyl, cyclopropyl, butyl, isobutyl, and the like. The term lower alkoxy means an alkoxy group containing a lower alkyl group.

The reaction of the lower alkoxy-2-methylaniline or lower alkoxy-2-methyl-N-sulfinylaniline and the alkyl- or aryl-sulfinylsulfonamide can be carried out thermally or in the presence of a tertiary amine catalyst. In either case an inert solvent can optionally be used. The tertiary amine catalyst can serve as the solvent. If the reaction is carried out thermally without added catalyst, one equivalent of the lower alkoxy-2-methylaniline or one equivalent of the lower alkoxy-2-methyl-N-sulfinylaniline is mixed with 2 to 5 or 1 to 5 equivalents of the sulfinylsulfonamide, respectively, and optionally with an inert solvent having a boiling point at atmospheric pressure of at least 120° C. The mixture is heated in a temperature range of 120° to 180° C. in a time interval of 15 minutes to 100 hours. Below 120° the reaction is very slow; above 180°, extensive decomposition occurs. Examples of inert solvents which can be employed include aliphatic hydrocarbons having a boiling point from about 50° to about 200° C., optionally substituted with halogen, phenyl, or alkoxy groups, such as 1,2-dipropoxyethane, and mononuclear or dinuclear aromatic hydrocarbons optionally substituted with halogen, lower alkyl, or nitro groups such as xylene or nitrobenzene. Advantageously, the reaction can be carried out in the presence of a tertiary amine catalyst, in which case the temperature required to obtain a reasonable reaction rate is markedly lowered, while decomposition reactions and other undesirable side-reactions are reduced. When a tertiary amine catalyst is employed, inert solvents as described hereinabove can have boiling points at atmospheric pressure as low as 50° C. Benzene and tetrahydrofuran are examples of such useful, inert solvents. The tertiary amine catalyst itself can also be used as the sole solvent.

In a typical reaction, one equivalent of the lower alkoxy-2-methyl-N-sulfinylaniline or one equivalent of the lower alkoxy-2-methylaniline is admixed with 1 to 4 equivalents or 2 to 4 equivalents, respectively, of the sulfinylsulfonamide, 0.5 to 4 equivalents of tertiary amine catalyst, an inert solvent, and the mixture is heated in the temperature range of 50° to 150° C., preferably at 60° to 90° C. for a period of time ranging from 15 minutes to 100 hours or more. If desired, one can use more than 4 equivalents of sulfinylsulfonamide for each equivalent of the lower alkoxy-2-methyl-N-sulfinylaniline or the lower alkoxy-2-methylaniline; but this is usually of little advantage and is economically wasteful. In another typical example, one equivalent of the lower alkoxy-2-methylaniline or one equivalent of the lower alkoxy-2-methyl-N-sulfinylaniline is admixed with 2 to 4 equivalents or 1 to 4 equivalents, respectively, of the sulfinylsulfonamide, and a sufficient quantity of a liquid tertiary amine having a boiling point at atmospheric pressure of 50° to 150° C. to act as both solvent and catalyst. The mixture is then heated in the temperature range of 50° to 150° C. for a period of time ranging from 15 minutes to 100 or more hours. Tertiary amines which can be used advantageously in the reaction are nitrogen-containing heteroaryl aromatic compounds such as pyridine, pyrazine, or quinoline, trialkyl tertiary amines; aryldialkylamines, and the like.

In the second reaction the alkoxy group of the lower alkoxy-2,1-benzisothiazole is converted to a hydroxy group by reaction with a suitable acid which can effect ether cleavage such as boron tribromide. An inert solvent is optional for this reaction.

In the final reaction the hydroxy-2,1-benzisothiazole is converted to the N-lower alkylcarbamoyloxy-2,1-benzisothiazole by reaction with a lower alkylisocyanate or it is converted to the N,N-di-lower alkylcarbamoyloxy-2,1-benzisothiazole by reaction with a lower dialkylcarbamoyl halide, preferably the chloride. This reaction is preferably carried out in a suitable, inert solvent which does not react with the carbamate function such as acetone, benzene, toluene, diethyl ether, acetonitrile, and the like. A catalyst for the reaction is not required, however, the reaction rate can be significantly accelerated by the use of a suitable tertiary amine catalyst such as triethyl amine, triethylenediamine, and the like, and/or a suitable organic tin catalyst such as stannous octoate, and the like.

The sulfinylsulfonamides can be prepared according to the procedure of G. Kresze, et al. (Angew. Chem. Intern. Ed. Engl., 1, 89 (1962) by refluxing a mixture of the sulfonamide, a slight excess of thionyl chloride, and dry benzene. In the case of the preparation of N-sulfinylmethanesulfonamide, however, I have found it unnecessary to reflux the reaction mixture several days as recommended by Kresze, et al. A reaction time of three to 17 hours is sufficient to obtain a good yield of N-sulfinylmethanesulfonamide.

The lower alkoxy-2-methyl-N-sulfinylanilines were prepared according to the procedure of G. Kresze, et al by refluxing a mixture of a lower alkoxy-2-methylaniline, a slight excess of thionyl chloride, and dry benzene for a period of time ranging from 30 minutes to 24 hours, then removing benzene from the mixture by evaporation, usually on a rotatory evaporator. Liquid products were distilled in vacuo, usually at 5 to 0.2 mm. Hg. Solid products were recrystallized from benzene or hexane.

The 2,1-benzisothiazolyl N-lower alkyl- or N,N-di-lower alkylcarbamates can be formulated with conventional additives, extenders, liquid or solid dispersants, and the like, in the preparation of pesticidal compositions. Those compounds which contain the defined carbamoyloxy group in the 4- or 7-position are preferred in pesticidal applications, particularly against Arthropoda. since they are not used full strength, they can be incorporated in those adjuvants and carriers conventionally employed with this general class of pesticide for facilitating the dispersion of the active ingredients. These toxicants can be applied, for example, as sprays, dusts, granules or baits, with the appropriate selection being dependent upon the type of pest and the environment. Formulations of these compounds can be in the form of dilute solutions, emulsifiable concentrates, wettable powders, granules, and the like.

The dusts are formed as admixtures of the active components and one or more finely divided solids, such as attapulgite clay, kieselguhr, pyrophyllite, talc, chalk, diatomaceous earth, calcium phosphates, calcium or magnesium carbonate, sulfur, lime, flours, and other organic or inorganic powdery solids which can function as dispersants and carriers for the active ingredients.

The pesticidal compounds can be made into liquid concentrates by solution or emulsion in suitable liquids, and into solid concentrates by admixture with talc, clays and other known solid carriers used in the pesticide art. The concentrates are compositions containing about 5–50 percent toxicant and the rest inert material which includes dispersing agents, emulsifying agents, and wetting agents. The concentrates are preferably diluted with water or other suitable liquid for spray application or with additonal solid carrier for use as dusts. Typical carriers for solid concentrates include fuller's earth, kaolin clays, silicas, and other highly absorbent, readily wet table inorganic diluents.

Useful liquid concentrates include the soluble and emulsifiable concentrates. They are liquid or paste compositions which can be readily dispersed in water or other suitable dispersant. The liquid concentrate may consist of the toxicant and a liquid or solid emulsifying agent, and optionally a liquid carrier, such as xylene, heavy aromatic naphthas and other nonvolatile organic solvents. For application these concentrates are dispersed in water or other liquid carrier, and normally applied as a spray to concentrate the area to be treated. Emulsifying or dispersing agents which are typically useful in pesticidal formulations in suitable concentration include the alkyl and alkylaryl sulfonates, their alkali metal salts, the alkylamide sulfonates, the alkylaryl polyether alcohols, the sulfated higher alcohols, the polyvinyl alcohols, polyethylene oxides, sulfonated animal, vegetable or mineral oils, the fatty acid esters of polyhydric alcohols and their ethylene oxide addition products and the like.

The concentration of the toxicant for control of insect and other pests can normally be in the range of about 0.001 percent up to about one percent, or higher when preferred, provided that an effective amount is employed for each specified formulation and use. A wide variation in the compositions useful for the pesticidal applications of these 2,1-benzisothiazolyl N-lower alkyl- or N,N-di-lower alkylcarbamates is additionally apparent from the decompositions which are known in the related pesticide art.

The following examples are set out to illustrate the novel compositions of the invention and to provide a better understanding of their details and advantages. In the following examples all nuclear magnetic resonance (nmr) spectra were recorded in deuteriochloroform solution in parts per million ($\delta$) relative to the internal reference standard tetramethylsilane. All temperatures are in degrees centigrade.

EXAMPLE 1

A mixture of 53.4 g. methanesulfonamide, 60 ml. thionyl chloride, and 90 ml. dry benzene was stirred magnetically and heated at reflux temperature 17 hours under a condenser fitted with a calcium sulfate drying tube. After cooling, benzene was removed from the mixture by evaporation on a rotatory evaporator and the residue was distilled to give 64.6 g. of N-sulfinylmethanesulfonamide as a yellow liquid, bp. 86°–88° at 0.75 mm. Hg. This material reacts violently with water, and care should be taken to protect it from atmospheric moisture which will rapidly hydrolyze it to methanesulfonamide. It can be safely stored under dry nitrogen at room temperature for several months in a closed glass container.

EXAMPLE 2

Preparation of 4-methoxy-2,1-benzisothiazole

A mixture of 24.1 g (0.1317 mole) 3-methoxy-2-methyl-N-sulfinylaniline, 22.6 g. (0.16) mole) N-sulfinylmethanesulfonamide, 9.5 g. (0.12 mole) dry pyridine, and 150 ml. dry benzene was prepared according to the procedure of Example 5, then stirred and heated at reflux temperature 60 hours under a reflux condenser fitted with calcium sulfate drying tube. After removing benzene and pyridine by evaporation on a rotatory evaporator, 100 ml. water was added to the reaction mixture which was then allowed to stand one hour at room temperature with occasional swirling. The mixture was extracted with chloroform; the chloroform extract was washed once with water and dried over calcium sulfate. After removing calcium sulfate by filtration, and evaporating chloroform from the filtrate, the black, oily residue was distilled to give 10.1 g. of a mixture of 3-methoxy-2-methylaniline and 4-methoxy-2,1-benzisothiazole, boiling range 82°–93° at 0.8–1.0 mm. Hg. Water (50 ml.) was added to the distillate. To this was added 40 ml. 25 percent aqueous hydrochloric acid. A yellow precipitate appeared in the mixture. Additional water was added until the precipitate dissolved, and the mixture was extracted with ether. The ether extract was washed once with water, then dried, filtered, and evaporated as before to give 6.3 g. (29.0 percent) of pure 4-methoxy-2,1-benzisothiazole as a light yellow oil. This structure was confirmed by its nmr spectrum which showed a singlet absorption at 9.32 ppm. for the proton attached to the 3-position of the benzisothiazole ring, a multiplet absorption spread between 7.55 and 7.15 ppm. for the 6- and 7-protons, a doublet absorption (showing meta splitting) centered at 6.33 ppm. (J=6) for the 5-proton, and a singlet absorption at 3.90 ppm. for the methoxy protons.

Analysis. Calcd. for $C_8H_7NOS$ (percent): C, 58.16; H, 4.27; N, 8.48; O, 9.68; S, 19.41. Found (percent) C, 58.07; H, 4.31; N, 8.59; O, 9.82; S, 19.06.

EXAMPLE 3

Preparation of 4-methoxy-2,1-benzisothiazole

A mixture of 19.5 g. (0.142 mole) 3-methoxy-2-methylaniline, 80.1 g. (0.568 mole) N-sulfinylmethanesulfonamide, 22.5 g. (0.284 mole) dry pyridine, and 210 ml. dry benzene was prepared and refluxed 65 hours with stirring. After completion of the reflux period, benzene and pyridine were removed from the reaction mixture by evaporation on a rotatory evaporator at 15–20 mm. Hg. and 50 ml. water was added to the residue. After standing 30 minutes at room temperature with occasional swirling, the mixture was extracted with chloroform. The chloroform extract was washed once with water and dried over calcium sulfate. Calcium sulfate was removed by filtration and chloroform was evaporated from the filtrate to give a dark, oil residue. The crude, tarry residue obtained from the chloroform extract of the reaction mixture was distilled to give 4.2 g. (17.9 percent) 4-methoxy-2,1-benzisothiazole as a light yellow oil, bp. 91° at 0.45 mm. Hg. This structure was confirmed by its nmr spectrum.

EXAMPLE 4

Preparation of 4-hydroxy-2,1-benzisothiazole

A mixture of 6.3 g. 4-methoxy-2,1-benzisothiazole, 28.5 g. boron tribromide, and 180 ml. methylene chloride was heated at reflux temperature 17 hours to give 5.1 g. 4-hydroxy-2,1-benzisothiazole as a yellow solid, mp. 184.5°–186.5° after recrystallization from benzene. This structure was confirmed by nmr.

Preparation of 7-methoxy-2,1-benzisothiazole

To a solution of 60.4 g. (0.33 mole) 2-methoxy-6-methyl-N-sulfinylaniline and 150 ml. dry benzene in a 1 liter single-neck round-bottom flask was added at room temperature a solution of 50.8 g. (0.36 mole) N-sulfinylmethanesulfonamide and 75 ml. dry benzene. The mixture was chilled in a ice bath while to it was added portionwise with swirling, a solution of 24.5 g. (0.31 mole) dry pyridine and 75 ml. dry benzene. A solid, crystalline material precipitated. The crystalline mass was broken up and the mixture was heated gently to boiling with constant swirling under a condenser fitted with a calcium sulfate drying tube until the solid dissolved (about 10 minutes). The mixture was then heated at reflux temperature 72 hours. After cooling, benzene and pyridine were removed from the mixture by evaporation on a rotatory evaporator and 300 ml. water was added to the residue. After standing at room temperature for 30 minutes with occasional swirling, the mixture was extracted with chloroform. The chloroform extract was washed once with water and dried over calcium sulfate. Calcium sulfate was removed by filtration and chloroform was removed from the filtrate by evaporation on a rotatory evaporator. The dark, oily residue was distilled in vacuo. After a small fore-cut, there was obtained 14.1 g. of 2-methoxy-6-methylaniline, bp. 62°–65° at 0.4–0.5 mm. Hg., containing by nmr a trace of 7-methoxy-2,1-benzisothiazole; 2.6 g. of an intermediate distillation fraction which was a mixture of 2-methoxy-6-methylaniline and 7-methoxy-2,1-benzisothiazole; and 21.3 g. (39.1 percent) of essentially pure 7-methoxy-2,1-benzisothiazole as a yellow oil, bp. 88°–93° at 0.3 mm. Hg. This structure was confirmed by its nmr spectrum which showed a singlet absorption at 9.06 ppm. for the proton attached to the 3-position of the benzisothiazole ring, a multiplet absorption spread between 7.37 and 6.47 ppm. for the benzenoid protons, and a singlet absorption at 3.97 ppm. for the methoxy protons.

Analysis — Calcd. for $C_8H_7NOS$ (percent): C, 58.16; H, 4.27; N, 8.48; S, 19.41. Found (percent): C, 58.05; H, 4.57; N, 8.59; S, 19.31.

EXAMPLE 6

Preparation of 7-hydroxy-2,1-benzisothiazole

7-Methoxy-2,1-benzisothiazole was dissolved in ether and converted to the hydrochloride using dry hydrogen chloride gas. The 7-methoxy-2,1-benzisothiazole hydrochloride (6.0 g.) was refluxed 22 hours in a solution of 16 g. boron tribromide and 160 ml. methylene chloride to give 3.78 g. pure, yellow, crystalline 7-hydroxy-2,1-benzisothiazole, mp. 99°–100.5° after recrystallization from hexane. This structure was confirmed by nmr.

EXAMPLE 7

Preparation of 5-methoxy-2,1-benzisothiazole

A mixture of 20.0 g. (0.11 mole) 4-methoxy-2-methyl-N-sulfinylaniline, 22.6 g. (0.16 mole) N-sulfinylmethanesulfonamide, 7.9 g. (0.10 mole) dry pyridine, and 150 ml. dry benzene was prepared according to the procedure of Example 5 and then stirred and heated at reflux temperature 60 hours under a condenser fitted with a calcium sulfate drying tube. Benzene and pyridine were removed from the mixture by evaporation on a rotatory evaporator. Water (100 ml.) was added to the residue and the mixture was allowed to stand one hour at room temperature with occasional swirling. The mixture was then extracted with chloroform and the chloroform extract was washed once with water and dried over calcium sulfate. Calcium sulfate was removed by filtration and chloroform was removed from the filtrate by evaporation on a rotatory evaporator. The black, oily residue was distilled to give 14.0 g. (77 percent) of 5-methoxy-2,1-benzisothiazole as a yellow oil, bp. 91°–98° at 0.7–0.8 mm. Hg. Its nmr spectrum showed to be essentially pure product, uncontaminated with starting materials. A second distillation of the product, bp. 92°–94° at 0.7 mm. Hg. gave 5-methoxy-2,1-benzisothiazole as a yellow solid, mp. 51°–55°. This structure was confirmed by its nmr spectrum which showed a singlet absorption at 8.75 ppm. for the proton attached to the 3-position of the benzisothiazole ring, a doublet absorption centered at 7.65 ppm. (J=9) for the 7-proton, a doublet absorption (showing meta splitting) centered at 7.07 ppm. (J=9) for the 6-proton, a singlet absorption (showing meta splitting) at 6.76 ppm. for the 4-proton, and a singlet absorption at 3.70 ppm. for the methoxy protons.

Analysis. — Calcd. for $C_8H_7NOS$ (percent): C, 58.16; H, 4.27; N, 8.48; O, 9.68; S, 19.41. Found (percent): C, 58.37; H, 4.25; N, 8.47; O, 9.85; S, 19.35.

EXAMPLE 8

Preparation of 5-methoxy-2,1-benzisothiazole

A mixture of 9.1 g. (0.05 mole) 4-methoxy-2-methyl-N-sulfinylaniline and 20.0 g. (0.1 mole) N-sulfinylbenzenesulfonamide was heated at 150°–160° for 30 minutes, cooled to room temperature, and diluted with about 50 ml. of water. The mixture was extracted with chloroform and the chloroform extract was dried over calcium sulfate. Calcium sulfate was removed by filtration and chloroform was evaporated from the filtrate to give an oily residue which was shown by nmr to be a mixture of 4-methoxy-2-methyl-N-sulfinylaniline and 5-methoxy-2,1-benzisothiazole.

EXAMPLE 9

Preparation of 5-methoxy-2,1-benzisothiazole.

A mixture of 6.7 g. (0.0406 mole) 4-methoxy-2-methylaniline, 22.6 g. (0.16 mole) N-sulfinylmethanesulfonamide, 6.3 g. (0.08 mole) dry pyridine, and 70 ml. dry benzene was prepared and heated with stirring at reflux temperature for 65 hours. After completion of the reflux period, benzene and pyridine were removed from the reaction mixture by evaporation on a rotatory evaporator at 15-20 mm. Hg. and 50 ml. water was added to the residue. After standing 30 minutes at room temperature, the mixture was extracted with chloroform. The chloroform extract was washed once with water and dried over calcium sulfate. Calcium sulfate was removed by filtration and chloroform was evaporated from the filtrate to give an oily residue. This was distilled to give 5.86 g. (87.5 percent) of pale yellow 5-methoxy-2,1-benzisothiazole, bp. 94° C. at 0.3 mm. Hg., which solidified at 49°-52° C. The structure was confirmed by its nmr spectrum.

EXAMPLE 10

Preparation of 5-hydroxy-2,1-benzisothiazole

5-Methoxy-2,1-benzisothiazole (6.3 g.) was refluxed 17 hours in a solution of 28.5 g. boron tribromide and 180 ml. methylene chloride to give 5.2 g. of 5-hydroxy-2,1-benzisothiazole as a green solid, mp. 215°-216° C. This structure was confirmed by nmr.

EXAMPLE 11

Preparation of 2,1-benzisothiazole-4-yl N-methylcarbamate

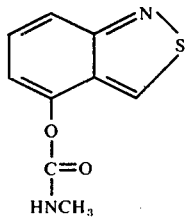

A solution of 2.0 g. 4-hydroxy-2,1-benzisothiazole, 2.0 g. methylisocyanate, catalytic amounts of triethylenediamine and stannous octoate, and 25 ml. dry tetrahydrofuran was allowed to stand in a closed container overnight at room temperature, then heated under a condenser at reflux temperature one hour. Solvent and excess methylisocyanate were removed from the mixture by evaporation on a rotatory evaporator. The solid residue was washed with hot hexane and isolated by suction filtration to give 3.1 g. 2,1-benzisothiazol-4-yl N-methylcarbamate, mp. 149°-152° after recrystallization from benzene. This structure was confirmed by nmr.

EXAMPLE 12

Pesticidal activity of 2,1-benzisothiazol-4-yl N-methylcarbamate

A. Nasturtium plants growing in a 5 ounce "Dixie" cup were infested with bean aphidS (*Aphis fabae*) and sprayed with 25 ml. of a solution containing water, small amounts of acetone and surfactant; and 500 ppm. 2,1-benzisothiazol-4-yl N-methylcarbamate. After 24 hours the carbamate had destroyed 100 percent of the bean aphids.

B. Lima bean plants growing in a 5 ounce "Dixie" cup were infested with two spotted mites (*Tetranychus urticae*) and sprayed with 25 ml. of the solution described above. After 48 hours, only minor damage to the mites were evident.

C. Lima bean plant leaves, sprayed with 25 ml. of the solution described above were placed in a petri dish with five Mexican bean beetle larvae (*Epilachna varivestus*). After 48 hours the carbamate had destroyed 100 percent of the Mexican bean beetle larvae. An identical procedure was used against southern armyworm (*Prodenia eridania*), whereby three of five of the southern armyworms were destroyed.

D. The toxicity of 2,1-benzisothiazol-4-yl N-methylcarbamate to F-58-WT strain houseflies was determined by applying a one microliter dose of an acetone solution of the carbamate to each of 25 flies. At the same time, an identical procedure was used except the carbamate was replaced with the commercial insecticide, DDT. Results of this test are given in Table I.

Table I

| Concentration of active substances (%) | 2,1-benz.[a] | DDT |
| --- | --- | --- |
| 1.0 | 88/100[b] | 88/92[b] |
| 0.5 | 92/96 | 92/100 |
| 0.25 | 76/84 | 68/84 |
| 0.125 | 60/72 | 56/64 |
| 0.06 | 32/40 | 24/44 |
| 0.03 | 32/32 | 0/32 |
| 0.015 | 16/12 | 0/24 |

[a]2,1-benzisothiazol-4-yl N-methylcarbamate.
[b]% knockdown of houseflies after 30 min./% kill after 24 hours.

EXAMPLE 13

Preparation and pesticidal activity of 2,1-benzisothiazol-7-yl-N-methylcarbamate To a solution of 2.0 g. 7-hydroxy-2,1-benzisothiazole, 40 ml. dry benzene, and catalytic amounts of triethylenediamine and stannous octoate was added 2.5 g. methylisocyanate. After about five minutes at room temperature, yellow solid carbamate product crystallized from solution. The mixture was allowed to stand at room temperature overnight, then solvent and excess methylisocyanate were removed by evaporation on a rotatory evaporator. The solid residue was washed with hot hexane and isolated by suction filtration to give 2.6 g. yellow, microcrystalline 2,1-benzisothiazol-7-yl N-methylcarbamate, mp. 145°-148° (dec.) after recrystallization from benzene. This structure was confirmed by ir and nmr. The insecticidal activity of this material was determined exactly as described in Example 12, whereby 2,1-benzisothiazol-7-yl N-methylcarbamate (500 ppm. concentration) destroyed 100 percent of Mexican bean beetle larvae and bean aphids, four of five southern armyworms, and had no effect on two-spotted mites.

EXAMPLE 14

Preparation and pesticidal activity of 2,1-benzisothiazol-4-yl N,N-dimethylcarbamate To a solution of 0.5 g. 4-hydroxy-2,1-benzisothiazole and 20 ml. dimethylformamide was added 0.4 g. of a 57 percent oil dispersion of sodium hydride at room temperature. After evolution of hydrogen from the mixture was completed, 1.1 g. dimethylcarbamoyl chloride was added and the mixture was stirred 16 hours at room temperature. Water (50 ml.) was added to the mixture, which was then extracted with chloroform. The chloroform extract was washed once with water and dried over calcium sulfate. Calcium sulfate was removed by filtration, and chloroform and dimethylformamide were evaporated from the filtrate in vacuo to give an oily residue. This was washed with hexane to give oily 2,1-benzisothiazol-4-yl N,N-dimethylcarbamate. This structure was confirmed by nmr. The insecticidal activity of this material was determined exactly as described in Example 12, whereby 2,1-benzisothiazole-4-yl N,N-dimethylcarbamate (500 ppm. concentration) destroyed 100 percent of bean aphides, two of five two-spotted mites, and had no effect on southern armyworms and Mexican bean beetle larvae.

In like manner, the 5- and 6-N-lower alkylcarbamates are made from the corresponding 5- and 6-hydroxy-2,1-benzisothiazoles. Also, the 4-, 5-, 6-, and 7-N,N-di-lower alkyl carbamates are made by the reaction of a di-lower alkylcarbamoyl chloride, for example, dimethylcarbamoyl chloride, with the corresponding 4-, 5-, 6-, and 7-hydroxy-2,1-benzisothiazoles.

It is to be understood that the above disclosure is by way of specific example and that numerous modifications and variations are available to those of ordinary skill in the art without departing from the true spirit and scope of my invention.

I claim:

1. A compound having the general formula

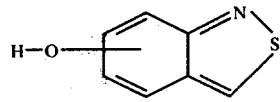

2. 4-Hydroxy-2,1-benzisothiazole in accordance with claim 1.
3. 5-Hydroxy-2,1-benzisothiazole in accordance with claim 1.
4. 6-Hydroxy-2,1-benzisothiazole in accordance with claim 1.
5. 7-Hydroxy-2,1-benzisothiazole in accordance with claim 1.

* * * * *

UNITED STATES PATENT AND TRADEMARK OFFICE
CERTIFICATE OF CORRECTION

PATENT NO. : 3,997,548
DATED : December 14, 1976
INVENTOR(S) : Gary M. Singerman It is certified that error appears in the above-identified patent and that said Letters Patent are hereby corrected as shown below:

```
Col. 3, line 11, "since" should read --Since--.
Col. 3, line 19, "powders, granules," should read
                 --powders, dusting powders, granules,--.
Col. 3, line 37, "additonal" should read --additional--.
Col. 3, line 65, "applications" should read --application--.
Col. 3, line 67, "decompositions" should read --compositions--.
Col. 4, line 36, "with calcium" should read --with a calcium--.
Col. 5, line 18, "oil" should read --oily--.
Col. 5, after line 32, insert "EXAMPLE 5".
Col. 5, line 40, "in a ice" should read --in an ice--.
Col. 6, line 43, "showed to" should read --showed it to--.
Col. 8, line 6, "aphidS" should read --aphids--.
Col. 8, line 16, "were" should read --was--.
```

Signed and Sealed this

Twenty-second Day of March 1977

[SEAL]

Attest:

RUTH C. MASON
*Attesting Officer*

C. MARSHALL DANN
*Commissioner of Patents and Trademarks*